United States Patent
Goebel et al.

[11] Patent Number: 5,458,923
[45] Date of Patent: Oct. 17, 1995

[54] PROCESS FOR IMPREGNATING A BUILDING MATERIAL WITH AN ORGANOSILICON COMPOUND

[75] Inventors: Thomas Goebel, Hanau; Rudolf Michel, Freigericht; Harald Alff, Kahl am Main; Josef Karl, Alzenau-Hoerstein, all of Germany

[73] Assignee: Degussa Aktiengesellschaft, Frankfurt am Main, Germany

[21] Appl. No.: 305,046

[22] Filed: Sep. 13, 1994

Related U.S. Application Data

[62] Division of Ser. No. 198,569, Feb. 18, 1994, abandoned, which is a division of Ser. No. 902,882, Jun. 23, 1992, Pat. No. 5,314,533.

[30] Foreign Application Priority Data

Jul. 5, 1991 [DE] Germany .......................... 41 22 263.6

[51] Int. Cl.⁶ .............................. B05D 3/02; B05D 5/12; C09D 183/00
[52] U.S. Cl. ........................................ 427/387; 427/393.6
[58] Field of Search ................................. 427/393.4, 387, 427/388.4, 393.6

[56] References Cited

U.S. PATENT DOCUMENTS

| | | | |
|---|---|---|---|
| 3,133,111 | 5/1964 | Wheeler, Jr. . | |
| 4,170,690 | 10/1979 | Armbruster et al. | 427/393.6 |
| 4,273,813 | 6/1981 | Meddaugh | 427/393.6 |
| 4,486,476 | 12/1984 | Fritsch et al. | 427/387 |
| 4,489,176 | 12/1984 | Kluth et al. | 427/387 |
| 4,517,240 | 5/1985 | Tracton et al. | 427/387 |
| 4,617,412 | 10/1986 | Green et al. . | |
| 4,661,551 | 4/1987 | Mayer et al. . | |
| 4,827,008 | 5/1989 | Gousetis et al. . | |
| 4,940,743 | 7/1990 | Grape et al. | 524/377 |
| 4,960,615 | 10/1990 | Stout et al. | 427/387 |
| 4,990,377 | 2/1991 | Wilson | 427/387 |
| 5,068,277 | 11/1991 | Vukov et al. | 427/393.6 |
| 5,075,140 | 12/1991 | Stout et al. | 427/393.6 |
| 5,110,684 | 5/1992 | Cooper | 427/393.6 |
| 5,171,476 | 12/1992 | Bloodworth et al. . | |

FOREIGN PATENT DOCUMENTS

| | | |
|---|---|---|
| 0234024 | 9/1987 | European Pat. Off. . |
| 0340816 | 11/1989 | European Pat. Off. . |
| 0416402 | 3/1991 | European Pat. Off. . |
| 2029446 | 12/1971 | Germany . |
| 2751714 | 2/1979 | Germany . |

*Primary Examiner*—Diana Dudash
*Attorney, Agent, or Firm*—Beveridge, DeGrandi, Weilacher & Young

[57] ABSTRACT

Aqueous emulsions are disclosed containing organosilicon compounds for the impregnation of inorganic materials, in particular building materials, containing alkoxysilanes and silane surfactants. The aqueous emulsions are storage stable and are adjusted to pH of from 3 to 5.5 just prior to use.

12 Claims, No Drawings

PROCESS FOR IMPREGNATING A BUILDING MATERIAL WITH AN ORGANOSILICON COMPOUND

This application is a divisional of application Ser. No. 08/198,569 filed on Feb. 18, 1994, now abandoned, which application is a divisional of prior application Ser. No. 07/902,882 filed on Jun. 23, 1992, now U.S. Pat. No. 5,314,533, which issued on May 24, 1994. Each of these priority applications is entirely incorporated herein by reference.

INTRODUCTION AND BACKGROUND

The present application relates to aqueous emulsions containing organosilicon compounds suitable for the impregnation of inorganic materials, and in particular for the impregnation of building materials. In another aspect, the present invention relates to the preparation of the special organosilicon compounds and to the use of the emulsions produced thereby.

Whereas in the past substances used for impregnating brickwork, concrete, etc. frequently contained organic solvents (DE-PS 20 29 446), this is being increasingly avoided in more recent developments. For example, DE-PS 27 51 714 relates to an impregnating agent for porous materials, consisting of an emulsion of alkoxysilanes in water or in water/alcohol mixtures and containing a surfactant as emulsifying agent. These agents, however, frequently have the disadvantage that the addition of surfactant reduces the hydrophobicizing effect of the alkoxysilane. Moreover, these agents have insufficient depth of penetration. The introduction of water-soluble groups into polysiloxanes (so-called "silicone surfactants") according to U.S. Pat. No. 4,661,551 results in microemulsions which can be diluted to any desired degree. However, these must be applied after 12 to 24 hours.

European Patent Applications EP-A 234 024 and EP-A-340 816 describe silane-containing aqueous emulsions which can be prepared with the addition of certain surfactants. Emulsions according to EP-A-340 816 in addition contain a substance which buffers the pH for the purpose of increasing the stability in storage.

SUMMARY OF THE INVENTION

It is an object of the present invention to provide emulsions as impregnating agents for inorganic materials, in particular building materials, which are more effective than the agents known in the art. A feature of the invention resides in aqueous emulsions containing organosilicon compounds for the impregnation of building materials, optionally containing anionic surfactants and substances which buffer the pH, characterized in that they contain from 1 to 80% by weight, in particular from 1 to 60% by weight, based on the total quantity, of at least one alkoxysilane corresponding to the following formula

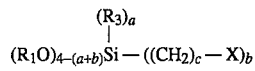

in which $R_1 = C_1-C_3$-alkyl, $R_3 = C_1-C_{20}$-alkyl, straight chain or branched, in particular $C_1-C_{10}$-alkyl, or phenyl, $X = H, Cl, Br, I, NH_2, SCN, CN, N_3, NHR, NR_2, \oplus NR_3, S_x$, aryl or alkenyl, preferably H or Cl, a=0 or 1 and b=1 or 2 and a+b is preferably equal to 1 or 2, and x and c=an integer from 1 to 6.

In addition, the emulsions of the invention contain from 1 to 20% by weight, preferably from 1 to 5% by weight, of an organosilicon compound corresponding to the following formula

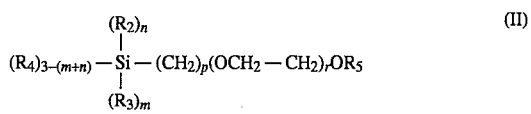

in which $R_2$ and $R_3$, which may be identical or different, denote $C_1-C_{20}$-alkyl, straight chain or branched, in particular $C_1-C_{10}$-alkyl, or phenyl, $R_4 = C_1-C_3$-alkoxy,

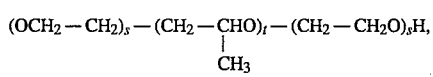

$R_5$=H, $C_1-C_{20}$-alkyl, $C_2-C_{36}$-alkenyl, $C_5-C_8$-cycloalkyl, $C_7-C_{36}$-aralkyl, in particular benzyl and phenyl groups substituted by alkyl groups, the alkyl groups being optionally branched, and when p=0 and r=0 then $OR_5$ stands for:

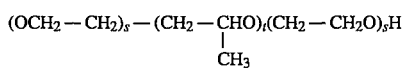

where s=3-50 and t=3-25 m=0, 1 or 2 and n=0, 1 or 2 under the condition that:

when p=0, then (m+n)=1 or 2 and when p≠0, then (m+n)=0, 1 or 2;

p=0, 1, 2, or 3 and r=an integer from 0 to 50.

Still further, the emulsions of the invention contain water in a quantity of from 1 to 95% by weight, preferably 1 to 75% by weight, the quantities by weight of all materials adding up, of course, to 100%.

The emulsions may contain not only the compounds corresponding to Formula (I) but also their condensation products, e.g. their dimers, trimers or other oligomers well known to the person skilled in the art.

The pH of the emulsion is preferably adjusted to about 7.5. In a preferred embodiment, a buffer is added to the emulsion in a quantity of from 0.1 to 5% by weight, based on the total quantity of the emulsion. This buffer may be, for example, sodium bicarbonate, sodium carbonate or trisodiumphosphate.

In a preferred embodiment, from 0.2 to 8.0% by weight, based on the total weight of the emulsion, of one or more of the known anionic surfactants are also added to the emulsion.

The emulsion according to the invention may also contain from 0.1 to 1.0% by weight of a known thickener, e.g. from the class of cellulose or starch derivatives, also based on the total quantity of the emulsion.

Emulsions which are particularly suitable as impregnating agents are those containing compounds corresponding to the Formula (II) in which:

(m+n)=0 or 1 when p≠0, and (m+n)=1 when p=0.

Compounds of Formula II are new and are also a feature of the invention. Compounds of the type in which p=0 and (m+n)=2 are described in EP-A- 416 402. According to the EP Application, they are prepared in organic solvents in the presence of bases.

In a further aspect, the present invention also relates to a new process for the preparation of organosilicon compounds corresponding to the Formula (II) in which p=0, characterized in that a compound corresponding to the following general formula

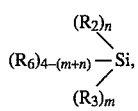 (III)

in which $R_6=C_1-C_3$-alkoxy and $R_2$, $R_3$, m and n have the meanings indicated above is reacted with a compound containing reactive hydrogen corresponding to the following general formula

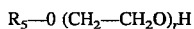 (IV)

in which $R_5$ and r have he meanings indicated above at the reflux temperature of the reaction mixture and at a pH of from 3.5 to 5.5, in particular of about 5.

No organic solvent is required. The procedure generally is carried out by adjusting the organosilane and the surfactant to the required pH with a small quantity of an acid, e.g. HCl and then heating until the reflux temperature has been reached. The reaction will also proceed at lower temperatures but more slowly. After the end of the reaction, the alcohol liberated, which is in most cases methanol or ethanol, is evaporated off. The surfactant is generally used in equimolar quantities, preferably in an excess of from 0.1 to 5 mol-%, and one or two alkoxy groups may be replaced by the surfactant.

The compounds corresponding to formula (II) in which p=0 may also be prepared by the process known from EP-A-416 402.

The invention further relates to a process for the preparation of organosilicon compounds corresponding to the formula (II) in which p=1, 2 or 3, characterized in that a compound corresponding to the following general formula

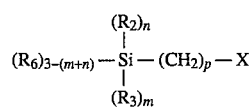 (V)

in which $R_2$, $R_3$, $R_6$, m, n and p have the meanings indicated above (with the exclusion of p=0) and X stands for Cl is reacted in an inert organic solvent with a sodium alcoholate corresponding to the following formula

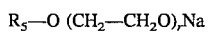 (VI)

in which $R_5$ and r have the meanings indicated above at 20 to 100° C., preferably at the reflux temperature, and the precipitated NaCl is then filtered off and the solvent is evaporated off. In one variation of this process, the surfactant is introduced into the reaction vessel in an inert organic solvent, e.g. an aliphatic, cycloaliphatic or aromatic hydrocarbon, and the sodium is then introduced, preferably in an equimolar quantity, and the formation of alcoholate with evolution of hydrogen is started by heating to 90° C. After the sodium had undergone complete reaction, the reaction mixture is preferably cooled to room temperature and the organosilicon compound corresponding to formula (V) is added dropwise, preferably in an equimolar quantity. The NaCl precipitates after the reaction mixture has been heated to 50° to 60° C. The required compound is then obtained after removal of the salt by filtration and removal of the solvent. According to the process previously described, the product obtained may then be reacted with another surfactant, which need not be identical with the one initially substituted. These compounds are new and are also claimed here.

Alternatively, the surfactant may be reacted with sodium methylate to produce the compound corresponding to formula (VI).

DETAILED DESCRIPTION OF THE INVENTION

The functional silicon surfactants of this invention are distinguished by their pronounced emulsifying action, in particularly in the pH range of from 6 to 9. The emulsions prepared with the aid of these surfactants are found to be stable for weeks in this pH range. For certain fields of application, these surfactants according to the invention must be split up into surface inactive fragments as soon as the organosilane emulsion has fulfilled its purpose. The stability of an emulsion must be adapted to its purpose. It is not always desirable to produce a very stable emulsion. For numerous fields of application, however, the emulsion is required to be stable under quite specific conditions and then decompose (break up) into its components when its purpose has been fulfilled. The emulsions claimed serve to alter the surface properties of porous inorganic materials, e.g. natural fillers (wollastonite, talc, etc.) and pulverulent silica or silicates so that these materials can be used for special applications in the rubber, bitumen and polymer field as designer made fillers. The alkoxysilanes in particular may be used to impart water repellence to building materials, brickwork, concrete and facades. In a preferred embodiment, an acid catalyst is added to the emulsions shortly before use, in particular to emulsions containing silanes having short chain, e.g. $C_3$- to $C_4$-alkylene groups. The catalyst must be capable of breaking the Si—0 bonds in the alkoxysilanes claimed, but not the Si—C bonds, thereby increasing the effectiveness of the silanes on neutral, slightly acid or alkaline substrates, in particular substrates which are problematic.

In a special embodiment, structurally viscous liquids can be produced by using the silicon functional surfactants corresponding to the formulae

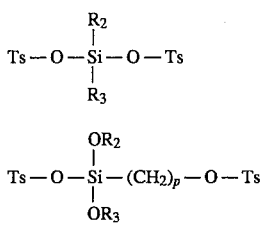

$$Ts-O-\underset{\underset{R_3}{|}}{\overset{\overset{R_2}{|}}{Si}}-O-Ts \quad \text{(VII)}$$

$$Ts-O-\underset{\underset{OR_3}{|}}{\overset{\overset{OR_2}{|}}{Si}}-(CH_2)_p-O-Ts \quad \text{(VIII)}$$

in which $R_2$, $R_3$ and p have the meanings indicated above and Ts corresponds to:

$(CH_2CH_2O)_n-R_5$  $\qquad$ n=3–15, $(CH_2CH_2O)_n-O-R_5$  $\qquad$ n=3–15 or

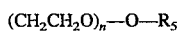

$m = 3$–$50 n = 25$.

These structurally viscous liquids render the addition of viscosity increasing agents superfluous and do not deleteriously affect the profile of properties required if they are applied in a diluted form. The stability and the physical-chemical properties for use of these emulsions as well as their technological properties depend on skillful choice of the functional silicon surfactant(s) used, the ionic surfactant(s) and to a large extent on the quantitative ratio of the hydrophobic to the hydrophilic portions of the molecule and on the pH.

It is known to the person skilled in the art that a reaction between alkali and silica takes place, especially in concrete, when silica-containing aggregates which are sensitive to alkalies react with alkali metal hydroxide. The alkalies are frequently carried into the concrete from outside by substances which assist thawing (e.g. NaCl). In unfavorable circumstances, the alkali metal silicate-hydrate-gels produced from the reaction between alkali and silica may cause cracking and bursting even to the point of breakdown of the concrete structure. The hydro-emulsions according to the invention which contain organosilane compounds and to which 3-sulphopropylsilanetriol (Si285) is added as alkali buffer for buffering to a pH of 3–5.5, preferably before their application to the building materials, are capable in particular of protecting concrete against the reaction between alkali and silica.

EXAMPLES

Example 1

Preparation of the organosilicon compounds corresponding to Formula (II) by the process according to the invention. General Method of Procedure:

The alkoxysilane and the surfactant or mixture of surfactants are mixed together in equimolar quantities or with an excess of surfactant of from 0.1 to 5 mol-% and the mixture is adjusted to pH of approximately 5 with an acid, in particular hydrochloric acid. The reaction mixture is heated to the reflux temperature and the reaction is left to proceed, the temperature continuously decreasing in the process. After the end of the reaction, the alcohol formed is drawn off under vacuum. Yields of ≧97% are generally obtained. It is also possible, however, to prepare these compounds from the corresponding chlorosilane compounds by the process known in the art.

One or more surfactants or an alcohol are used in equimolar quantities or preferably in an excess of from 0.1 to 5 mol-%, depending on the proportion of chlorine atoms which are to be replaced by a molecule of surfacant or an alkoxy group. It is helpful but not essential for the reaction to add an equimolar quantity of an organic base (e.g. triethylamine) based on the number of chlorine atoms. The hydrochloride which precipitates is then filtered off so that the inert solvent (e.g. toluene) can be distilled off.

Tables 1 and 2 show the compounds prepared according to the invention, which will hereinafter be referred to as silicon surfactants.

TABLE 1

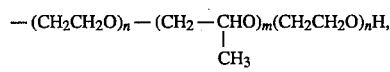

| Surfactant | SL-Nomenclature |
|---|---|
| —(CH₂—CH₂O)₁₀—⟨phenyl⟩—C₈H₁₇ | SL 51-0-12 |
| —(CH₂—CH₂O)₁₀—C₁₃H₂₇ | SL 51-0-14 |
| —(CH₂—CH₂O)₈—⟨phenyl⟩—C₉H₁₉ | SL 51-0-16 |
| —(CH₂—CH₂O)₆—(CH₂)ₓ—CH=CH—(CH₂)ₓ—CH₃ | SL 51-0-17 |

TABLE 2

$$\text{Surfactant} - O - \underset{\underset{OC_2H_5}{|}}{\overset{\overset{OC_2H_5}{|}}{Si}} - (CH_2)_2 - CH_3$$

| Surfactant | SL-Nomenclature |
|---|---|
| $-(CH_2-CH_2O)_{10}-\phenyl-C_8H_{17}$ | SL 51-0-11 |
| $-(CH_2-CH_2O)_8-C_{13}H_{27}$ | SL 51-0-13 |
| $-(CH_2-CH_2O)_{11}-\phenyl-C_9H_{19}$ | SL 51-0-15 |
| $-(CH_2-CH_2O)_{10}-C_{13}H_{27}$ | SL 51-0-18 |
| $-(CH_2-CH_2O)_5-(CH_2)_x-CH=CH-(CH_2)_x-CH_3$ (x: 6 · 10) | SL 51-0-19 |

Example 2

In the same way was the compounds of the following type $$\text{Surfactant} - O - \underset{\underset{OR}{|}}{\overset{\overset{OR}{|}}{Si}} - \text{Alkyl},$$

$$\text{Surfactant} - O - \underset{\underset{CH_3}{|}}{\overset{\overset{CH_3}{|}}{Si}} - O - \text{Surfactant}$$

so also the silanes which are substituted with two surfactant molecules may be prepared from the corresponding dichlorosilanes or dialkoxysilanes as described in the previous Example.

Table 3 shows the compounds of the following structure obtained:

TABLE 3

$$\text{Surfactant} - O - \underset{\underset{CH_3}{|}}{\overset{\overset{CH_3}{|}}{Si}} - O - \text{Surfactant}$$

| Surfactant | SL-Nomenclature |
|---|---|
| $-(CH_2-CH_2O)_{10}-C_{13}H_{27}$ | SL 51-0-20 |
| $-(CH_2-CH_2O)_{10}-\phenyl-C(CH_3)_2-CH_2-C(CH_3)_3$ | SL 51-0-21 |
| $-(CH_2-CH_2O)_6-\phenyl-C_9H_{19}$ | SL 51-0-22 |
| $-(CH_2-CH_2O)_5-(CH_2)_7-CH_3$ | SL 51-0-24 |

TABLE 3-continued $$\text{Surfactant} - O - \underset{\underset{CH_3}{|}}{\overset{\overset{CH_3}{|}}{Si}} - O - \text{Surfactant}$$

| Surfactant | SL-Nomenclature |
|---|---|
| —(CH$_2$—CH$_2$O)$_{10}$—⟨C$_6$H$_4$⟩—C$_9$H$_{19}$ | SL 51-0-27 |
| —(CH$_2$—CH$_2$O)$_{15}$—⟨C$_6$H$_4$⟩—C$_9$H$_{19}$ | SL 51-0-41 |

Example 3

The preparation of silicon surfactants of the following type:

$$\text{RO} - \underset{\underset{OR}{|}}{\overset{\overset{OR}{|}}{Si}} - (CH_2)_3 - O - \text{Surfactant}$$

is demonstrated in this Example.

If the process is carried out in ethanol, the sodium is first dissolved to form sodium ethanolate and an equimolar quantity of the surfactant, based on the alkali metal, is then added and the reaction mixture is heated, preferably to the reflux temperature.

The reaction is completed after about 2 hours; the reaction mixture is cooled and 30-chloropropyltriethoxysilane is introduced dropwise into the clear solution. The solution is then heated 50°–65° C. The reaction is completed after 1 to 2 hours at this temperature. The precipitated NaCl is filtered off after cooling and the alcohol is separated by distillation. The reactions are complete.

In another variation, the surfactant is introduced into the reaction vessel in an inert organic solvent, e.g. toluene, and the sodium is then introduced in approximately equimolar quantities to produce the surfactant-O—Na compound directly. The reaction is completed after 1 to 2 hours at 70° to 80° C.

The reaction mixture is cooled to room temperature and chloropropyl-triethoxysilane is added dropwise to the clear solution. The reaction mixture is then heated to 50°–65° C. The reaction is completed after about an hour at this temperature. After cooling, the precipitated NaCl is filtered off and the toluene is distilled off under vacuum.

TABLE 4

$$\text{RO} - \underset{\underset{OR}{|}}{\overset{\overset{OR}{|}}{Si}} - (CH_2)_3 - O - \text{Surfactant}$$

| Surfactant | R | SL-Nomenclature |
|---|---|---|
| —(CH$_2$—CH$_2$O)$_5$—(CH$_2$)$_7$—CH$_3$ | CH$_3$— | SL 51-1-12 |
| —(CH$_2$—CH$_2$O)$_6$—⟨C$_6$H$_4$⟩—C$_9$H$_{19}$ | C$_2$H$_5$— | SL 51-2-14 |
| —(CH$_2$—CH$_2$O)$_{10}$—⟨C$_6$H$_4$⟩—C$_9$H$_{19}$ | C$_2$H$_5$— | SL 51-2-15 |

Preparation of the Emulsion

The dispersion apparatus known to the person skilled in the art (rotor-stator systems, high pressure homogenizers) are used for the preparation of the emulsion.

Example 4

Preparation of an Emulsion in Operation.

Starting materials: 40.00% of organosilane (or an organosilane system) (=Formula I); 58.40% of VE water; 1.25% of silicon surfactant (=Formula II); 0.35% of anionic surfactant (alkyl sulphonates, for example sodium octyl sulphonate) (VE=completely free from salt).

The following apparatuses are used for preparing the emulsion:

Container for starting mixture equipped with stirrer.

Feed pump for charging the high pressure homogenizer, with two-stage pressure release unit:

Heat exchanger for cooling the emulsion to 10°–20° C.

VE water and the total quantity of emulsifier (or pair of emulsifiers) are introduced with stirring into the container for the starting mixture.

After addition of the organosilane, the pH is adjusted to 7.5 by the addition of sodium bicarbonate.

Example 5

Preparation of an Emulsion in the Laboratory.

Components weighed in: 50 g of water; 0.12 g of NaHCO$_3$ (pH of the emulsion ~7.5); 1.37 g of silicon surfactant (Formula I); 33.3 g of organosilane (Formula II).

The components are successively weighted into a 50 ml reaction flask in the sequence in which they are listed above and are then homogenized for 3 minutes in an Ultraturrax (Rotor-Stator) at 18,000 revs/min. The emulsion may then be after-treated for one minute in an ultrasound bath with stirring (500 revs/min).

Appearance of the emulsion: milky.

Properties: dilutable in any proportions.

The emulsions thus prepared are stable for several weeks, i.e. no phase separation occurs ("formation of layer of cream").

If this does occur at any point, an emulsion suitable for use which has lost none of its effect is obtained by simple stirring.

The crude emulsion is pumped into the high pressure homogenizer by means of the feed pump and homogenized therein at 80–500 bar. After the emulsion has cooled to 10°–20° C., it is again homogenized at 100–700 bar. The reduction in pressure in the second pressure stage is 20%.

After the emulsion has again cooled to room temperature, it is filled into its contents.

Appearance of the Emulsion: milky.

Properties: dilutable in any proportions.

The emulsions thus prepared are stable for several months, i.e., no phase separation occurs ("formation of layer of cream"). If this does occur at any time, an emulsion ready for use which has lost none of its effect is obtained by simple stirring.

In a preferred method of preparing the emulsion, an ionic surfactant known per se is added. Substantially less energy is then required for preparing thermodynamically stable dispersions. In one particular embodiment, the ionic, preferably anionic surfactants are added to the organo-silane phase and the silicon-functional surfactants are added to the aqueous phase. The degree of penetration of the active materials depends not only on the porosity of the building materials and the care with which the emulsions are applied, but also on the particle size. Particles <1 µm are obtained by the combination of Si-functional surfactants and ionic surfactants. It is known to the person skilled in the art that the introduction of gas (generally air) during the preparation of the crude emulsion has a deleterious effect on the stability and may even lead to destruction of the dispersing apparatus.

There is therefore also the possibility of measuring the streams of educt (organosilane, Si-functional surfactant/water, ionic surfactants) directly into the homogenizer.

Assessment for technical application.

Samples of stone measure 5×5×5 cm are first conditioned for several weeks under normal atmospheric conditions (23° C., 50% relative humidity) and then weighed. 200 ml of the organosilane emulsions produced are introduced into a 400 ml glass beaker, and three weight samples are completely immersed twice for one minute at an interval of half an hour. After silanization has taken place, the stone samples are kept at room temperature for 14 days. The water absorption is determined according to DIN 12 103 by introducing two samples into a water bath covered with a column of water of 5 cm and the weight is checked after 10, 30 and 60 minutes and 2, 4, 8 and 24 hours. To measure the depth of penetration, the cubes of samples are broken up with a hammer and chisel and sprayed with water which has been colored with ink. The test for water repellency is an optical test and may be carried out by immersing the sample in water but generally by applying a droplet of water with a pipette to a horizontal contact surface.

The drop of water is shaken off after 15 minutes and the contact surface is assessed. The numbers by which the results are graded have the following meanings:

1. No wetting of the substrate surface
2. 50% Distribution of the water drop on the substrate surface without dark coloration.
3. Distribution over an area, i.e. complete wetting by the water drop together with slight darkening of the substrate surface.
4. Water partly drawn in and severe darkening of the contact surface.

The water absorption is an indication of the extent to which the hydrophobic treatment has been effective. The less water absorbed, the better is the hydrophobic treatment.

The depth of penetration is an indication of the depth to which an impregnating agent is effective in stone.

To illustrate the positive properties of the emulsions according to the invention, comparison tests were carried out with state of the art products. The product used in Experiment 1 was a commercial microemulsion based on siloxane (oligomeric alkoxysiloxanes) containing silicon-functional surfactants (silicone surfactants) having the following structure:

$$\text{Surfactant} - \text{O} - \underset{\underset{CH_3}{|}}{\overset{\overset{CH_3}{|}}{Si}}(\text{O} - \underset{\underset{CH_3}{|}}{\overset{\overset{CH_3}{|}}{Si}}) \underset{\underset{CH_3}{|}}{\overset{\overset{CH_3}{|}}{Si}} - CH_3$$

These products are generally copolymers of polysiloxane having one or more polyglycol ether chains. The product used in Experiment 2 was a commercial emulsion of organosilane and a mixture of surfactants according to EP-A-340 816.

$$H_3C-\underset{\underset{CH_3}{|}}{\overset{\overset{CH_3}{|}}{C}}-CH_2-\underset{\underset{CH_3}{|}}{\overset{\overset{CH_3}{|}}{C}}-\underset{}{\bigcirc}-[O\sim]_{9-10}OH \quad (1)$$

-continued

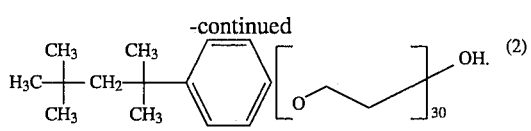

The experiments were carried out in two concentration stages which show that even when the emulsions according to the invention contain only a low concentration of active substance (5%), they produce significantly better results in water absorption and depth of penetration than the state of the art emulsions which have concentrations of active substance of 40%.

impregnation with the emulsion. The drying time is generally 72 hours at 105° C. Constancy of weight is considered to have been reached when the weight changes by not more than 0.1% within 24 hours. The stones are weighed after a cooling period of 2 hours at room temperature. 150 ml of impregnating solution are then applied over a period of 1 minute in a 400 ml glass beaker. The treatment is repeated after a storage time of 30 min. at room temperature. The water absorption is determined as described above, as are also the depth of penetration and the water repellency.

TABLE 5

Results on lime sandstone
(Blank test: Water absorption after 24 h: 12.30%)
Example 6

| Experiment | Active compound | Concentration of active compound (% by wt.) | Surfactant(s) | Water Absorption (%) after 24 h | Depth of penetration (mm) | Water Repellency |
|---|---|---|---|---|---|---|
| 1 | Siloxanes | 40 | Silicone surfactants | 0.98 | 2–3 | 1 |
|  |  | 10 |  | 0.82 | 0.5–2 | 1–2 |
| 2 | $C_8H_{17}Si(OC_2H_5)_3$ | 40 | Surfactants (1), (2) | 1.57 | 7–9 | 2 |
|  |  | 5 |  | 0.87 | 1–3 | 4 |
| 3 | $C_8H_{17}Si(OC_2H_5)_3$ | 40 | (SL 51-0-19) | 0.64 | 6–8 | 1–2 |
|  |  | 5 |  | 0.65 | 3–6 | 2 |
| 4 | $C_8H_{17}Si(OC_2H_5)_3$ | 40 | (SL 51-0-22) | 0.75 | 4–7 | 1 |
|  |  | 5 |  | 0.70 | 3–4 | 1–2 |
| 5 | $C_8H_{17}Si(OC_2H_5)_3$ | 40 | (SL 5-0-17 | 0.63 | 7–10 | 1 |
|  |  | 5 |  | 0.60 | 3–5 | 2 |

TABLE 6

Results on Höxter sandstone
(Blank test: Water absorption after 24 h: 3.86%)
Example 7

| Experiment | Active compound | Concentration of active compound (% by wt.) | Surfactant(s) | Water absorption (%) after 24 h | Depth of penetration (mm) | Water Repellency |
|---|---|---|---|---|---|---|
| 6 | Siloxanes | 10 | Silicone surfactants | 1.02 | 0–0.5 | 3 |
| 7 | $C_8H_{17}Si(OC_2H_5)_3$ | 10 | Surfactants (1) (2) | 3.11 | 3–4 | 4 |
| 8 | $C_8H_{17}Si(OC_2H_5)_3$ | 10 | (SL 51-0-22) | 1.15 | 4–5 | 3–4 |
| 9 | $C_3H_7Si(OC_2H_5)_3$ $C_{16}H_{33}Si(OC_2H_5)_3$ 1:1 | 10 | (SL 51-0-35) | 0.6 | 3–5 | 2–3 |

Experiments 8 and 9 show that an improved activity can be obtained even on neutral substances such as Höxter sandstone, especially when a combination of silanes consisting of short chain and long chain alkyl groups can be used.

Example 6

Cement Mortar.
The cubes of mortar are dried to constant weight before

TABLE 7

Results on cement mortar
(Blank test: Water absorption after 24 h: 7.13%)

| Experiment | Active compound | Concentration of active compound (% by wt.) | Surfactant(s) | Water absorption (%) after 24 h | Depth of penetration (mm) |
|---|---|---|---|---|---|
| 1 | Siloxanes | 10 | Silicone surfactants | 0.76 | 0–0.5 |
| 2 | $C_8H_{17}Si(OC_2H_5)_3$ | 40)* | Surfactants (1), | 1.01 | 6–8 |
|   |   | 10 | (2) | 0.49 | 1–2 |
| 3 | $C_8H_{17}Si(OC_2H_5)_3$ | 40 | (SL 51-0-19) | 0.50 | 5–9 |
|   |   | 10 |   | 0.42 | 1–3 |
| 4 | $C_8H_{17}Si(OC_2H_5)_3$ | 40 | (SL 51-0-22) | 0.45 | 3–10 |
|   |   | 10 |   | 0.43 | 1–5 |
| 5 | $C_8H_{17}Si(OC_2H_5)_3$ | 40 | (SL 5-0-17 | 0.38 | 4–6 |

*patchy on the stone

TABLE 8

Results on aerated concrete
(Blank test: Water absorption after 24 h: 65.07%)
Example 9

| Experiment | Active compound | Concentration of active compound (% by wt.) | Surfactant(s) | Water absorption (%) after 24 h | Depth of penetration (mm) |
|---|---|---|---|---|---|
| 1 | Siloxanes | 10 | Silicone surfactant | 11.04 | 4–6 |
| 2 | $C_8H_{17}Si(OC_2H_5)_3$ | 10 | Surfactants (1) (2) | 9.60 | 4–10 |
| 3 | $C_8H_{17}Si(OC_2H_5)_3$ | 10 | (SL 51-0-22) | 8.50 | 6–10 |
| 4 | $C_3H_7Si(OC_2H_5)_3$ $C_{16}H_{33}Si(OC_2H_5)_3$ | 10 | (SL 51-0-35) | 9.31 | 5–10 |

The water absorption and depth of penetration could be improved compared with those of commercial emulsions even on a building material with very large pores, such as aerated concrete.

Example 10

The hydrophobic properties are substantially improved by the addition of basic or acid catalysts. The addition of 3-sulphopropyl-trihydroxysilane (Si 285)

$$(HO)_3Si-CH_2CH_2CH_2-SO_3H$$

has proved to be particularly advantageous. The pH is adjusted to ~4 by lightly stirring this compound into the emulsion directly before its application.

TABLE 9

Results on Lime Sandstone.

| Experiment | Active compound | Concentration (% by wt.) | Surfactant | H$_2$O absorption after 24 h (%) |
|---|---|---|---|---|
| 1 | $C_3H_7Si(OC_2H_5)_3$ | 40 | (SL51-0-15) | 1.79 |
|   |   | 20 |   | 5.03 |
|   |   | 10 |   | 7.20 |
| 2 | $C_3H_7Si(OC_2H_5)_3$ (+ Si 285) | 40 | (SL51-0-5) | 0.72 |
|   |   | 20 |   | 0.73 |
|   |   | 10 |   | 0.75 |

The results obtained with the system according to the invention containing catalyst were good to very good compared with those previously obtained even if the active compound contained a short chain alkyl group, as in n-propyltriethoxysilane.

Aqueous emulsions containing organosilicon compounds are used for the impregnation of inorganic materials, in particular building materials.

Further variations and modifications of the foregoing invention will be apparent to those skilled in the art and are intended to be encompassed by the claims appended hereto.

German priority application P 41 22 267.6 is relied on and incorporated herein by reference.

We claim:

1. A process for the impregnation of a building material, comprising:

providing an aqueous organosilicon emulsion including:
(a) from 1 to 80% by weight of at least one alkoxysilane corresponding to formula (I) as follows:

$$(R_1O)_{4-(a+b)}Si-((CH_2)_c-X)_b \overset{(R_3)_a}{\underset{|}{}} \quad (I)$$

in which
$R_1$ is a $C_1$–$C_3$-alkyl group,
$R_3$ is a $C_1$–$C_{20}$-alkyl group, straight chain or branched, or a phenyl group,
X is a member selected from the group consisting of: H, Cl, Br, I, $NH_2$, SCN, CN, $N_3$, NHR, $N(R)_2$, $\oplus N(R)_3$, $-S_x-$, aryl and alkenyl,
a is 0 or 1,
b is 1 or 2, and
x and c each denotes an integer in the range from 1 to 6,
(b) from 1 to 30% by weight of an organosilicon compound corresponding to formula (II) as follows:

$$(R_4)_{3-(m+n)}-\underset{\underset{(R_3)_m}{|}}{\overset{\overset{(R_2)_n}{|}}{Si}}-(CH_2)_p(OCH_2-CH_2)_rOR_5 \quad (II)$$

in which

R$_2$ and R$_3$, which may be identical or different, each denotes a C$_1$–C$_{20}$-alkyl group, straight chain or branched, or a phenyl group, R$_4$ denotes a C$_1$–C$_3$-alkoxy group, (OCH$_2$—CH$_2$)$_r$ OR$_5$, or $$(OCH_2-CH_2)_s-(CH_2-\underset{\underset{CH_3}{|}}{CHO})_t-(CH_2-CH_2O)_sH,$$

wherein s is 3–50 and t is 3–25,

R$_5$ denotes H, a C$_1$–C$_{20}$-alkyl group, a C$_2$–C$_{36}$-alkenyl group, a C$_5$–C$_8$-cycloalkyl group or a C$_7$–C$_{36}$-aralkyl group, wherein when p is 0 and r is 0, OR$_5$ stands for: —(OCH$_2$—CH$_2$)$_s$—(CH$_2$—CHO)$_t$(CH$_2$—CH$_2$O)$_s$H;

m is 0, 1 or 2, and n is 0, 1 or 2, on the condition that when p is 0 then (m+n) is 1 or 2, and when p is not 0, then (m+n) is 0, 1 or 2;

p is 0, 1, 2 or 3, and r is an integer with a value from 0 to 50, and (c) water for the balance up to 100% by weight of the emulsion;

adjusting the pH of the emulsion to 3 to 5.5; and immediately thereafter applying said emulsion to the building material.

2. A process for the impregnation of a building material, comprising:

providing an aqueous organosilicon emulsion including:
(a) from 1 to 80% by weight of at least one alkoxysilane corresponding to formula (I) as follows:

$$(R_1O)_{4-(a+b)}\underset{\underset{}{|}}{\overset{\overset{(R_3)_a}{|}}{Si}}-((CH_2)_c-X)_b \quad (I)$$

in which

R$_1$ is a C$_1$–C$_3$-alkyl group,

R$_3$ is a C$_1$–C$_{20}$-alkyl group, straight chain or branched, or a phenyl group, X is a member selected from the group consisting of: H, Cl, Br, I, NH$_2$, SCN, CN, N$_3$, NHR, N(R)$_2$, $\oplus$N(R)$_3$, —S$_x$—, aryl and alkenyl, a is 0 or 1, b is 1 or 2, and x and c each denotes an integer in the range from 1 to 6, (b) from 1 to 30% by weight of an organosilicon compound corresponding to formula (II) as follows:

$$(R_4)_{3-(m+n)}-\underset{\underset{(R_3)_m}{|}}{\overset{\overset{(R_2)_n}{|}}{Si}}-(CH_2)_p(OCH_2-CH_2)_rOR_5 \quad (II)$$

in which

R$_2$ and R$_3$, which may be identical or different, each denotes a C$_1$–C$_{20}$-alkyl group, straight chain or branched, or a phenyl group, R$_4$ denotes a C$_1$–C$_3$-alkoxy group, (OCH$_2$—CH$_2$)$_r$OR$_5$, or $$(OCH_2-CH_2)_s-(CH_2-\underset{\underset{CH_3}{|}}{CHO})_t-(CH_2-CH_2O)_sH,$$

wherein s is 3–50 and t is 3–25,

R$_5$ denotes H, a C$_1$–C$_{20}$-alkyl group, a C$_2$–C$_{36}$-alkenyl group, a C$_5$–C$_8$-cycloalkyl group or a C$_7$–C$_{36}$-aralkyl group, wherein when p is 0 and r is 0, OR$_5$ stands for: —(OCH$_2$—CH$_2$)$_s$—(CH$_2$—CHO)$_t$(CH$_2$—CH$_2$O)$_s$H;

m is 0, 1 or 2, and n is 0, 1 or 2, on the condition that when p is 0, then (m+n) is 1 or 2, and when p is not 0, then (m+n) is 0, 1 or 2;

p is 0, 1, 2 or 3, and r is an integer with a value from 0 to 50, and (c) water for the balance up to 100% by weight of the emulsion;

adjusting the pH of the emulsion to 3 to 5.5 by adding 3-sulphopropyl-trihydroxysilane to said emulsion prior to applying said emulsion to said building material; and thereafter applying said emulsion to the building material.

3. The process according to claim 1, wherein the aqueous organosilicon emulsion additionally contains an anionic surfactant.

4. The process according to claim 1, wherein the aqueous organosilicon emulsion additionally contains a buffer.

5. The process according to claim 1, wherein in the aqueous organosilicon emulsion, R$_3$ in Formula (I) is a C$_1$ to C$_{10}$ alkyl group.

6. The process according to claim 1, wherein in the aqueous organosilicon emulsion, R$_2$ and R$_3$ in Formula (II) are each C$_1$ to C$_{10}$ alkyl groups.

7. The process according to claim 1, wherein the pH is adjusted to about 5.

8. The process according to claim 2, wherein the aqueous organosilicon emulsion additionally contains an anionic surfactant.

9. The process according to claim 2, wherein the aqueous organosilicon emulsion additionally contains a buffer.

10. The process according to claim 2, wherein in the aqueous organosilicon emulsion, R$_3$ in Formula (I) is a C$_1$ to C$_{10}$ alkyl group.

11. The process according to claim 2, wherein in the aqueous organosilicon emulsion, R$_2$ and R$_3$ in Formula (II) are each C$_1$ to C$_{10}$ alkyl groups.

12. The process according to claim 2, wherein the pH is adjusted to about 5.

\* \* \* \* \*